US005171838A

United States Patent [19]

Chiba

[11] Patent Number: 5,171,838

[45] Date of Patent: Dec. 15, 1992

[54] LEU3A BINDING PEPTIDES

[75] Inventor: Yukinobu Chiba, Tokyo, Japan

[73] Assignee: Kureha Kagaku Kogyo Kabushiki Kaisha, Tokyo, Japan

[21] Appl. No.: 526,921

[22] Filed: May 22, 1990

[30] Foreign Application Priority Data

Mar. 23, 1990 [JP] Japan .................................. 2-73895

[51] Int. Cl.[5] ........................ C07K 7/08; A61K 37/02

[52] U.S. Cl. ..................................... 530/326; 530/324

[58] Field of Search .................. 530/324, 326; 514/14, 514/12

[56] References Cited

FOREIGN PATENT DOCUMENTS 0330227 2/1989 European Pat. Off. .
0365209 10/1989 European Pat. Off. .
0341444 11/1989 European Pat. Off. .
WO87/03601 6/1987 PCT Int'l Appl. .
WO89/03222 4/1989 PCT Int'l Appl. .
WO89/03420 4/1989 PCT Int'l Appl. .
WO8903221 4/1989 PCT Int'l Appl. .
WO89/03813 5/1989 PCT Int'l Appl. .

OTHER PUBLICATIONS

Classon et al., *Proc. Natl. Acad. Sci. U.S.A.* 83: 4499–4503 (1986).
Sattentau et al., *Science* 23: 1120–1123 (1986).
Dalgleish et al., *The Lancet*, Nov. 7, 1987, pp. 1047–1050.
Landau et al., *Nature* 334: 159–162 (1988).
Jameson et al., *Science* 240: 1335–1339 (1988).
Peterson and Seed, *Cell* 54: 65–72 (1988).
Hayashi et al., *Arch. Virol.* 105: 129–135 (1989).
Maddon et al., *Cell*, vol. 42, 1985, pp. 93–104.

*Primary Examiner*—Lester L. Lee
*Assistant Examiner*—Avis Davenport
*Attorney, Agent, or Firm*—Arnold, White & Durkee

[57] ABSTRACT

Compositions comprising peptide analogues of a CD4 epitope capable of interacting with a monoclonal antibody designated Leu3a or with the envelope glycoprotein (gp120) of the human immunodeficiency virus (HIV) are provided. In a preferred embodiment, the peptide will consist of the amino acid sequence: ser-lys-leu-asn-asp-arg-ala-asp-ser-arg-arg-ser-leu-trp-asp. The invention also includes a series of peptides having one or more D-amino acid substitution that confer enhanced resistance to degradation in serum. Pharmaceutical compositions and methods for using the peptides in therapeutic applications are also provided.

17 Claims, 7 Drawing Sheets

( I ) R=H (2) (3) (5) (6) (8) (9) (11) (12) (14) (15)

Synthetic Scheme of R-Ser-Lys-Leu-Asn-Asp-Arg-Ala-Asp-Ser-Arg-Arg-Ser-Leu-Trp-Asp-OH (1)

```
              B    D    E    E    D              B
              |    |    |    |    |              |
         H-Ala-Asp-Ser-Arg-Arg-Ser-Leu-Trp-Asp-Resin   (27)
                        E
                        |
              ↑  A-Arg-C   (28)
              E    B    D    E    E    D              B
              |    |    |    |    |    |              |
         A-Arg-Ala-Asp-Ser-Arg-Arg-Ser-Leu-Trp-Asp-Resin   (29)
              ↓
              E    B    D    E    E    D              B
              |    |    |    |    |    |              |
         H-Arg-Ala-Asp-Ser-Arg-Arg-Ser-Leu-Trp-Asp-Resin   (30)
                   B
                   |
              ↑  A-Asp-C   (31)
```

(42) (43) (44) (45) (46)

(II) R=Fmoc

H-Lys-Leu-Asn-Asp-Arg-Ala-Asp-Ser-Arg-Arg-Ser-Leu-Trp-Asp-Resin (42)

D

↓ Fmoc-Ser-C (47)

D F B E B D E E D B

Fmoc-Ser-Lys-Leu-Asn-Asp-Arg-Ala-Asp-Ser-Arg-Arg-Ser-Leu Trp-Asp-Resin (48)

↓

Fmoc-Ser-Lys-Leu-Asn-Asp-Arg-Ala-Asp-Ser-Arg-Arg-Ser-Leu-Trp-Asp-OH (49)

A=Fmoc (9-Fluorenylmethyloxycarbonyl)

B-OBu$^t$ (tert-Butyl ester)

C=Symmetric Anhydride or HOBT Active Ester

D=Bu$^t$ (tert-Butyl)

E-Mtr (4-Methoxy-2,3,6-trimethylbenzenesulfonyl)

F=Boc (tert-Butoxycarbonyl)

G=OPfp (pentafluorophenyl ester)

LEU3A BINDING PEPTIDES

FIELD OF THE INVENTION

This invention relates to peptide analogues of a CD4 epitope, and, in particular, an epitope capable of interacting with a monoclonal antibody designated Leu3a or with the envelope glycoprotein (gp120) of the human immunodeficiency virus (HIV). The invention also includes a series of peptides having enhanced resistance to degradation in serum. Pharmaceutical compositions and methods for using the peptides in diagnostic and therapeutic applications are also provided.

DESCRIPTION OF THE RELATED ART

The CD4 molecule is a cell surface protein expressed by a subset of mature T-lymphocytes and macrophages. Stewart, et al., *J. Immunol.* 136:3773–3778 (1986). The CD4 molecule lymphocytes is a receptor for Class II major histocompatibility antigens. Littman D. R., *A. Rev. Immunol.* 5:561–584 (1987). The CD4 protein is encoded by a single gene and its sequence is highly conserved.

The CD4 protein is also the receptor for the human immunodeficiency virus, Type I (HIV-I), the causative agent of human Acquired Immunodeficiency Syndrome (AIDS). The gp120 envelope protein of the HIV interacts with CD4 , thereby potentiating entry of the virus into the cell. Dalgleish, et al., *Nature* 312:763–766 (1984); Klatzmann, et al., Science 225:59–63 (1984).

The CD4 molecule has been the object of intense investigation. During the past several years, the DNA encoding human CD4 has been cloned and sequenced and the amino acid sequence has been determined. The amino acid sequence is shown below (Table I).

TABLE I

| | | | | |
|---|---|---|---|---|
| 1 | KKVVLGKKGD | TVELTCTASQ | KKSIQFHWKN | 30 |
| 31 | SNQIKILGNQ | GSFLTKGPSK | LNDRADSRRS | 60 |
| 61 | LWDQGNFPLI | IKNLKIEDSD | TYICEVEDQK | 90 |
| 91 | EEVQLLVFGL | TANSDTHLLQ | GQSLTLTLES | 120 |
| 121 | PPGSSPSVQC | RSPRGKNIQG | GKTLSVSQLE | 150 |
| 151 | LQDSGTWTCT | VLQNQKKVEF | KIDIVVLAFQ | 180 |
| 181 | KASSIVYKKE | GEQVEFSFPL | AFTVEKLTGS | 210 |
| 211 | GELWWQAERA | SSSKSWITFD | LKNKEVSVKR | 240 |
| 241 | VTQDPKLQMG | KKLPLHLTLP | QALPQYAGSG | 270 |
| 271 | NLTLALEAKT | GKLHQEVNLV | VMRATQLQKN | 300 |
| 301 | LTCEVWGPTS | PKLMLSLKLE | NKEAKVSKRE | 330 |
| 331 | KAVWVLNPEA | GMWQCLLSDS | GQVLLESNIK | 360 |
| 361 | VLPTWSTPVQ | PMALIVLGGV | AGLLLFIGLG | 390 |
| 391 | IFFCVRCRHR | RRQAERMSQI | KRLLSEKKTC | 420 |
| 421 | QCPHRFQKTC | SPI | | 433 |

The CD4 amino acid sequence was corrected in 1988 by workers responsible for cloning the CD4 gene [Maddon, et al., Cell 42:93–104 (1985); Maddon, et al., Cell 55: 541 (1988)]. Therefore, one must correct sequences in references published without the benefit of the later changes to correspond to the new sequence and numbering scheme. Most sequences discussed here have been corrected to correspond to the new scheme. The letters have the following meaning in accordance with convention: A = alanine; R = arginine; N = asparagine; D = aspartic acid; C = cysteine; Q = glutamine; E = glutamic acid; G = glycine; H = histidine; I = isoleucine; L = leucine; K = Lysine; M = methionine; F = phenylalanine; P = proline; S = serine; T = threonine; W = tryptophan; Y = tyrosine; and V = valine.

A number of monoclonal antibodies that bind to the CD4 protein have been prepared and described in the literature. See, e.g., Sattentau, et al., *Science* 234:1120–1123 (1986). Investigators have attempted to locate particular peptide sequences within CD4 that are recognized by selected monoclonal antibodies and to correlate those epitopes with HIV-binding. Unfortunately, attempts to define the precise binding sites responsible for the HIV—CD4 interaction have not been wholly successful.

For example, Sattentau, et al., tested a number of anti-CD4 monoclonal antibodies for the ability to inhibit binding of other anti-CD4 monoclonal antibodies to the CD4 molecule and for the ability to block gp120 binding to the cell surface. From those studies, Sattentau, et al., concluded that two epitopes were important for gp120 binding: monoclonal antibodies OKT4A, Leu3a, EDU-2, T4/t19 Thy5d7, F101-5, F101-65, 94bl, 91D6, and MT310 reportedly fell into a family related to one important epitope; MT321, MT151, and VIT4 reportedly recognized a second important epitope. Other antibodies tested, including OKT4D, were said to recognize portions of the CD4 molecule that were considered less important in mediating the CD4-gp120 interaction. Sattentau, et al., did not prepare or test any synthetic peptides for antibody binding activity.

Later, Jameson, et al., *Science* 240:1335–1339 (1988), tested three peptides for the ability to inhibit HIV-induced cell syncytium formation. Jameson, et al., labeled the peptides 1–25, 25–58, and 40–72 respectively. 25–58 reportedly corresponded to the epitope bound by monoclonal antibody OKT4A, and 40–72 reportedly corresponded to the epitope bound by monoclonal antibody OKT4D. Only the peptide labeled 25–58 was reported to effectively inhibit HIV-induced syncytium formation. Jameson, et al., did not set forth the amino acid sequences of the peptides they tested.

In studies involving recombinant mouse-human chimeric molecules, Landau, et al., *Nature* 334:159–162 (1988), reported that gp120-CD4 interaction required human CD4 regions located between amino acids 37 and 83. Those investigators suggested that human CD4 binding of Leu3a required, at a minimum, amino acids 37–83 and that residues outside the 37–83 region contributed to the gp120 binding activity. Landau, et al., however, did not report tests for any synthetic peptides having the sequences mentioned.

In other studies, Reinherz, et al., International Patent Application W089/03222 (published Apr. 20, 1989), tested recombinant peptides for the ability to inhibit CD4-gp120 interaction and observed that a recombinant polypeptide comprising amino acids 1 through 110 was inactive. Reinherz concluded that at least two domains of the CD4 molecule were necessary for gp120 binding.

Lifson et al., International Patent Application WO/03221, published Apr. 20, 1989, report tests of synthetic peptides based on the CD4 sequence for ability to inhibit HIV-induced syncytium formation. Only one peptide—a peptide that had been derivatized at cysteine 84—was found to be an effective inhibitor of syncytium formation. The corresponding non-derivatized peptide was inactive.

From these studies and others like them, it is apparent that the study of peptide epitopes important in monoclonal antibody recognition and HIV-binding of CD4 was uncertain and unpredictable, and peptides capable of effectively inhibiting HIV-CD4 interaction continued to be highly sought after by those of skill in the art.

When tested in the competitive assay of Example I, for example, a Leu3a binding peptide of the present invention will exhibit an $IC_{50}$ below about 100 $\mu g$/well, and preferably, below about 80 $\mu g$/well. Even more preferred peptides will usually have an $IC_{50}$ that is less than about 60 $\mu g$/well, or, for the most highly preferred species, less than about 40 $\mu g$/well.

Preferably the peptide will include the sequence SKLNDRADSRRSLWD. More preferred are the peptides shown below in Table II. Even more preferred are peptides consisting essentially of the sequence SKLNDRADSRRSLWD and a peptide consisting of the sequence SKLNDRADSRRSLWD.

TABLE II

| |
|---|
| SKLNDRADSRRSLWD |
| PSKLNDRADSRRSLWD |
| GPSKLNDRADSRRSLWD |
| KGPSKLNDRADSRRSLWD |
| TKGPSKLNDRADSRRSLWD |
| LTKGPSKLNDRADSRRSLWD |
| FLTKGPSKLNDRADSRRSLWD |
| SFLTKGPSKLNDRADSRRSLWD |
| GSFLTKGPSKLNDRADSRRSLWD |
| QGSFLTKGPSKLNDRADSRRSLWD |
| NQGSFLTKGPSKLNDRADSRRSLWD |
| GNQGSFLTKGPSKLNDRADSRRSLWD |
| SKLNDRADSRRSLWDQ |
| PSKLNDRADSRRSLWDQ |
| GPSKLNDRADSRRSLWDQ |
| KGPSKLNDRADSRRSLWDQ |
| TKGPSKLNDRADSRRSLWDQ |
| LTKGPSKLNDRADSRRSLWDQ |
| FLTKGPSKLNDRADSRRSLWDQ |
| SFLTKGPSKLNDRADSRRSLWDQ |
| GSFLTKGPSKLNDRADSRRSLWDQ |
| QGSFLTKGPSKLNDRADSRRSLWDQ |
| NQGSFLTKGPSKLNDRADSRRSLWDQ |
| GNQGSFLTKGPSKLNDRADSRRSLWDQ |
| SKLNDRADSRRSLWDQG |
| PSKLNDRADSRRSLWDQG |
| GPSKLNDRADSRRSLWDQG |
| KGPSKLNDRADSRRSLWDQG |
| TKGPSKLNDRADSRRSLWDQG |
| LTKGPSKLNDRADSRRSLWDQG |
| FLTKGPSKLNDRADSRRSLWDQG |
| SFLTKGPSKLNDRADSRRSLWDQG |
| GSFLTKGPSKLNDRADSRRSLWDQG |
| QGSFLTKGPSKLNDRADSRRSLWDQG |
| NQGSFLTKGPSKLNDRADSRRSLWDQG |
| GNQGSFLTKGPSKLNDRADSRRSLWDQG |
| SKLNDRADSRRSLWDQGN |
| PSKLNDRADSRRSLWDQGN |
| GPSKLNDRADSRRSLWDQGN |
| KGPSKLNDRADSRRSLWDQGN |
| TKGPSKLNDRADSRRSLWDQGN |
| LTKGPSKLNDRADSRRSLWDQGN |
| FLTKGPSKLNDRADSRRSLWDQGN |
| SFLTKGPSKLNDRADSRRSLWDQGN |
| GSFLTKGPSKLNDRADSRRSLWDQGN |
| QGSFLTKGPSKLNDRADSRRSLWDQGN |
| NQGSFLTKGPSKLNDRADSRRSLWDQGN |
| GNQGSFLTKGPSKLNDRADSRRSLWDQGN |
| SKLNDRADSRRSLWDQGNF |
| PSKLNDRADSRRSLWDQGNF |
| GPSKLNDRADSRRSLWDQGNF |
| KGPSKLNDRADSRRSLWDQGNF |
| LTKGPSKLNDRADSRRSLWDQGNF |
| FLTKGPSKLNDRADSRRSLWDQGNF |
| SFLTKGPSKLNDRADSRRSLWDQGNF |
| GSFLTKGPSKLNDRADSRRSLWDQGNF |
| QGSFLTKGPSKLNDRADSRRSLWDQGNF |
| NQGSFLTKGPSKLNDRADSRRSLWDQGNF |
| GNQGSFLTKGPSKLNDRADSRRSLWDQGNF |

SUMMARY OF THE INVENTION

Fortunately, the surprising discovery has now been made that a series of novel peptides, which may comprise as few as 15 amino acids, are extremely potent inhibitors of CD4-Leu3a interaction, and are highly useful in the study of CD4-gp120 interaction. Therefore, in a general sense, the present invention relates to peptide derivatives of CD4 that bind to Leu3a; to peptide CD4 derivatives that bind gp120 of human immunodeficiency virus; and to peptide derivatives of CD4 that have enhanced serum stability. Methods of using the peptides for binding to Leu3a or gp120 are also provided.

In some embodiments, a peptide of the invention is referred to generally as a "Leu3a binding" peptide, which is defined here as a peptide that is capable of binding to the antigen binding site of the Leu3a antibody. The Leu3a binding activity of the peptide may be demonstrated by the ability of the peptide to competitively inhibit specific interactions between the human CD4 protein and the Leu3a monoclonal antibody when tested under suitable conditions for immunoassay.

Selected peptides of the invention will preferably comprise about 30 amino acids or fewer, and more preferably, about 20 amino acids or fewer. In many preferred embodiments, the peptides will include as few as about 15 amino acids. In certain cases, however, longer peptides may be preferred.

Novel peptide embodiments preferred for use in menstrual likely to contain peptide-degrading proteases, such as serum, plasma, or blood, are also provided by the invention. In those embodiments, the peptides may be modified to enhance stability by substitution with one or more D-amino acids, preferably from one to four D-amino acids, for the corresponding L-form found in the native CD4 polypeptide. Such modified peptides may be many times more resistant to proteolytic degradation than are corresponding peptides comprising only L-amino acids and are referred to here as "stabilized peptides." A "stabilized peptide" of the invention, at a minimum, will exhibit at least a two-fold enhancement in half-life in normal human serum, measured according to the protocol set forth in Example III.

Although it has been discovered that the effect of a particular amino acid substitution on Leu3a binding activity is often somewhat unpredictable, with the aid of the present disclosure, those of skill in the art will be able to prepare a number of peptides with the desired stability characteristics. For example, certain "key" residues, such as ala 55, may be readily substituted with the corresponding D-form without sacrifice of biologic activity. Accordingly, in preferred embodiments stabilized peptides include peptides comprising the sequence ser-lys-leu-asn-asp-arg-ala-asp-ser-arg-arg-ser-leu-trp-asp
49 50 51 52 53 54 55 56 57 58 59 60 61 62 63 wherein ala 55 is a D-amino acid and a second amino acid selected from the group consisting of ser, lys, leu, asn, arg, and trp is a D-amino acid. More preferably, however, the second amino acid is selected from the group consisting of lys 50, asn 52, ser 57, arg 58, or arg 59. In yet a further preferred embodiment, the peptide will contain more than two D-amino acids, for example, D-substitutions at lys 50, ala 55, and arg 59; lys 50, ala 55, and leu 61; or leu 51, ala 55, and leu 61. Alternatively, the stabilized peptide may have a single a D-amino acid substitution of asp 56.

For the purposes of the present invention, the term peptide includes pharmaceutically acceptable salts of one or more amino acid residues, also referred to in specific instances as peptide salts. The salt is a metal complex, in which metals are zinc, iron, calcium, magnesium, aluminum, etc.; a salt of acid such as hydrochloric acid, hydrobromic acid, sulfuric acid, phosphoric acid, tannic acid, oxalic acid, fumaric acid, gluconic acid, alginic acid, maleic acid, acetic acid, trifluoroacetic acid, citric acid, benzoic acid, succinic acid, malic acid, ascorbic acid, tartaric acid, etc; an alkali or alkaline earth metal salt such as sodium salt, potassium salt, calcium salt, magnesium salt,,etc.; or an ammonium salt.

The invention also includes peptides, including stabilized peptides, which bind to the gp120 glycoprotein of human immunodeficiency virus and block or inhibit CD4-gp120 interaction, and pharmaceutical compositions containing such peptides, including their pharmaceutically acceptable salts.

The peptides of the invention may be used in a variety of procedures to bind Leu3a monoclonal antibody, to bind a gp120 glycoprotein of a human immunodeficiency virus, to inhibit interaction between Leu3a and a CD4 molecule, or to inhibit interaction between CD4 and gp120. Accordingly, in preferred embodiments, the invention includes a method for binding Leu3a by contacting a preparation containing Leu3a with a peptide of the present invention; a method for binding gp120 by contacting a preparation containing gp120 with a peptide of the invention; a method for inhibiting binding of Leu3a to CD4 by contacting a preparation containing Leu3a and CD4 with a peptide of the invention; and a method of inhibiting interaction between CD4 and gp120 by contacting a preparation containing CD4 and gp120 with a peptide of the present invention. Of course, each of these procedures will be carried out under conditions suitable to allow binding between the peptide and the Leu3a or gp120 to occur. A variety of suitable conditions may be readily determined by those of skill in the art, including but not limited to, conditions where the ingredients are provided in an aqueous preparation having physiologic conditions of pH, ionic strength, etc, including, for example, biological samples such as blood or semen, and various other physiologic media such as phosphate buffered saline, or tissue culture medium. The proper ratio of ingredients necessary to achieve a desired degree of binding or inhibition may be determined by conventional procedures, e.g., titration of peptide, Leu3a, CD4, or gp120 to determine an effective binding concentration or ratio of each.

These and other aspects of the invention which will become more apparent from a description of particular embodiments when read in conjunction with the claims.

DESCRIPTION OF THE DRAWINGS

FIG. 2A–F Scheme of Peptide Synthesis

DETAILED DESCRIPTION OF THE INVENTION

Figure 1:
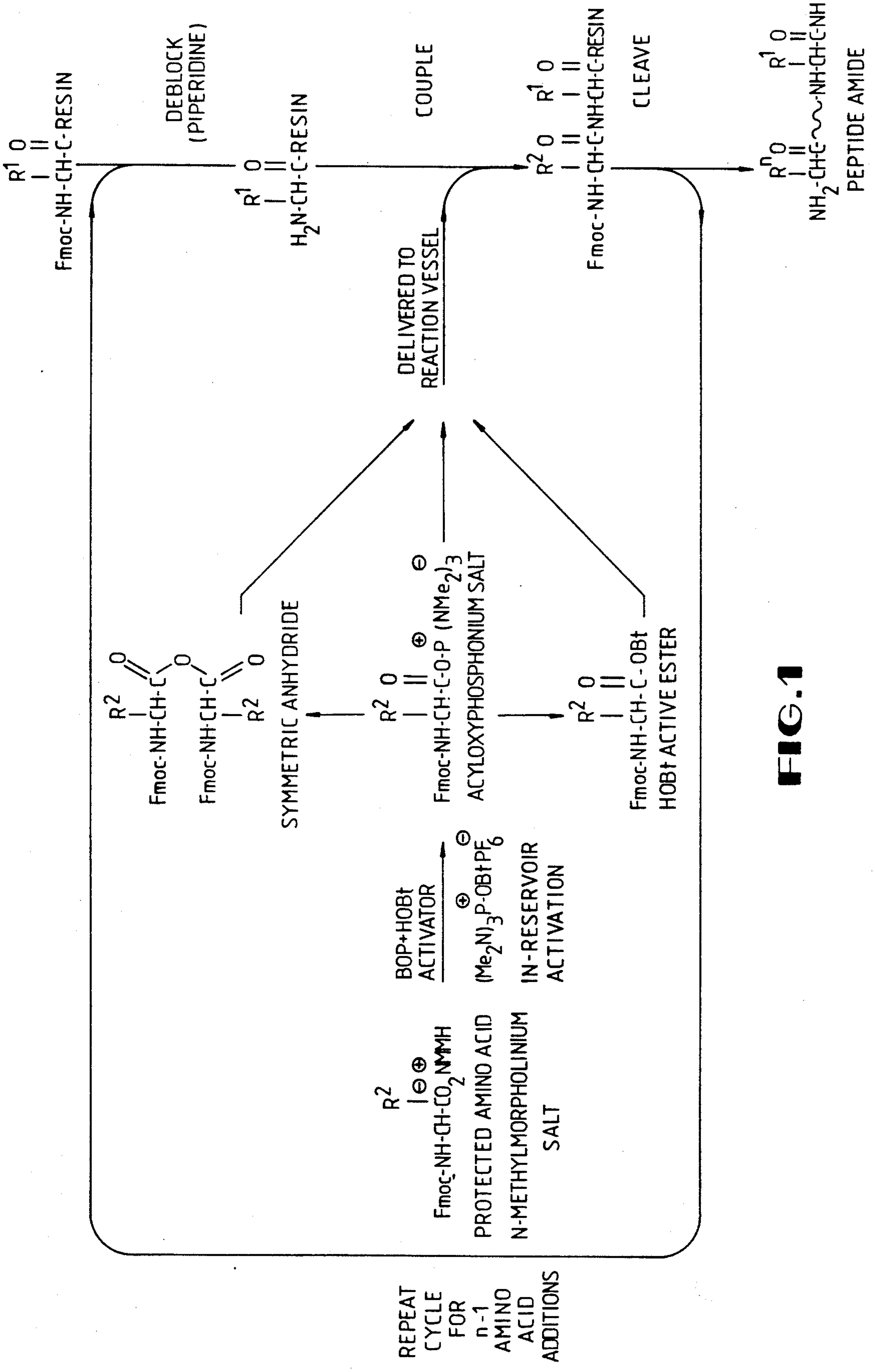
FIG. 1 Fmoc Synthesis Cycle with BOP/HOBt In-Reservoir Activation
Figure 2A:
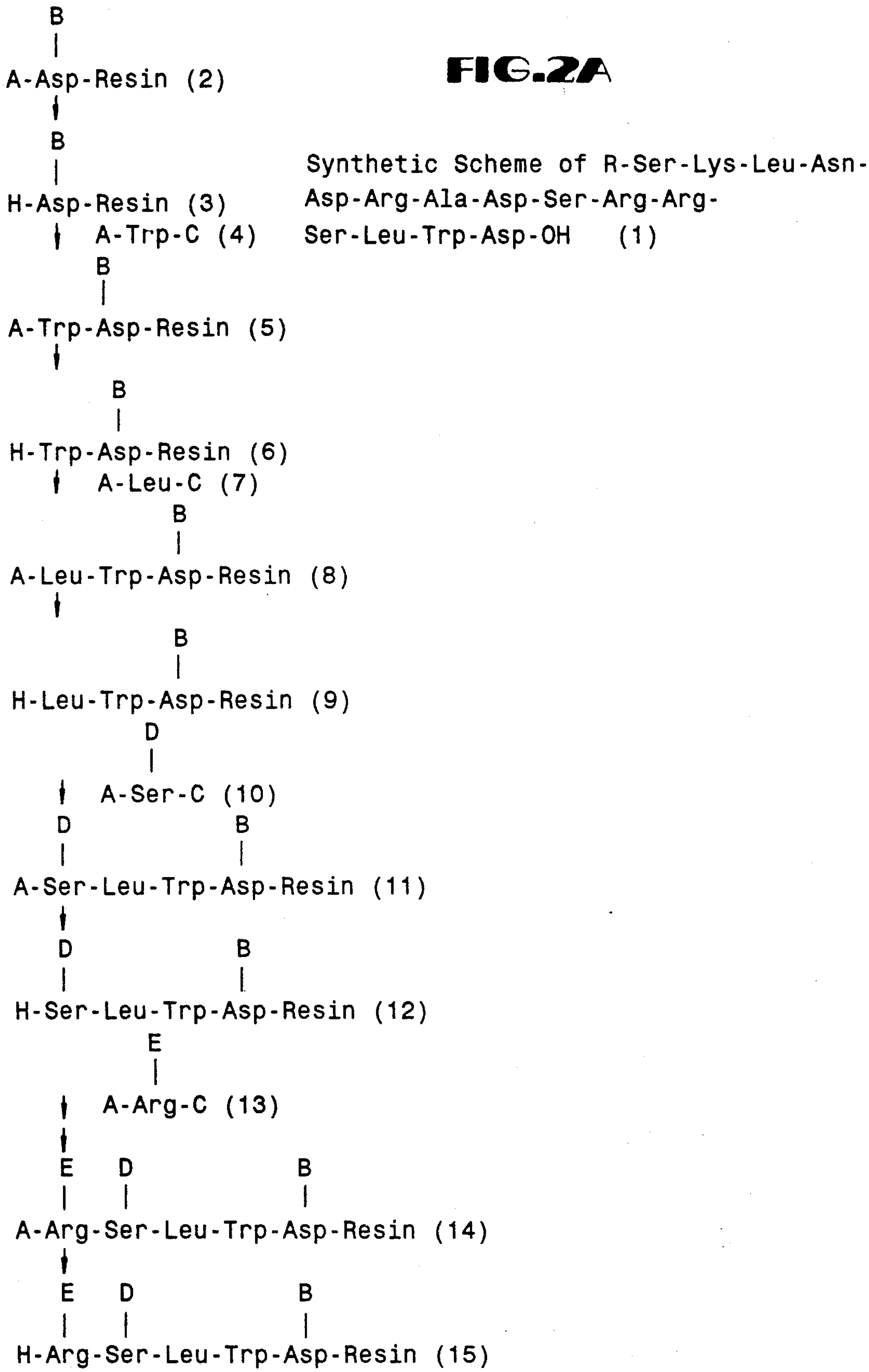
Figure 2B:
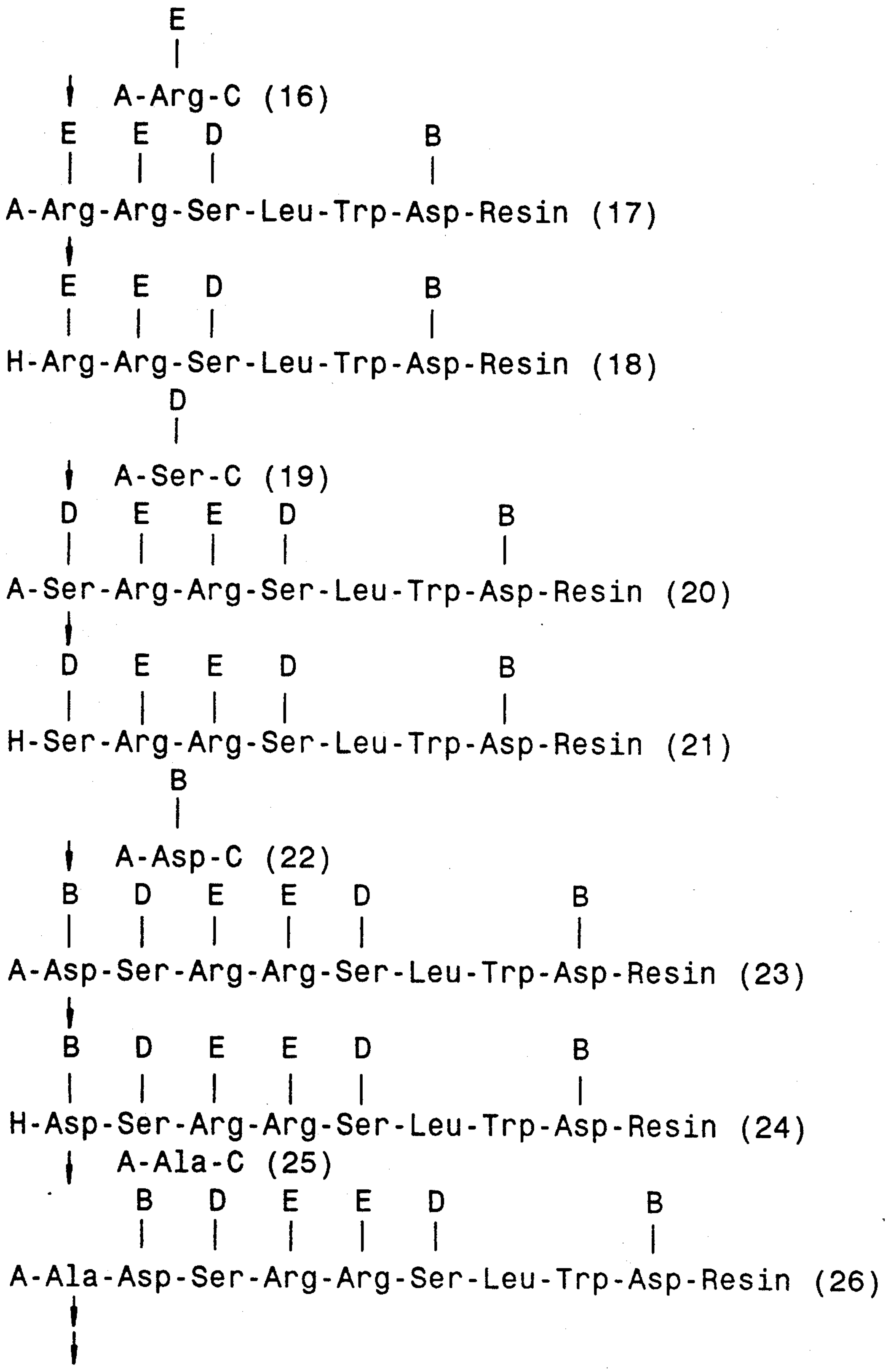
Figure 2C:
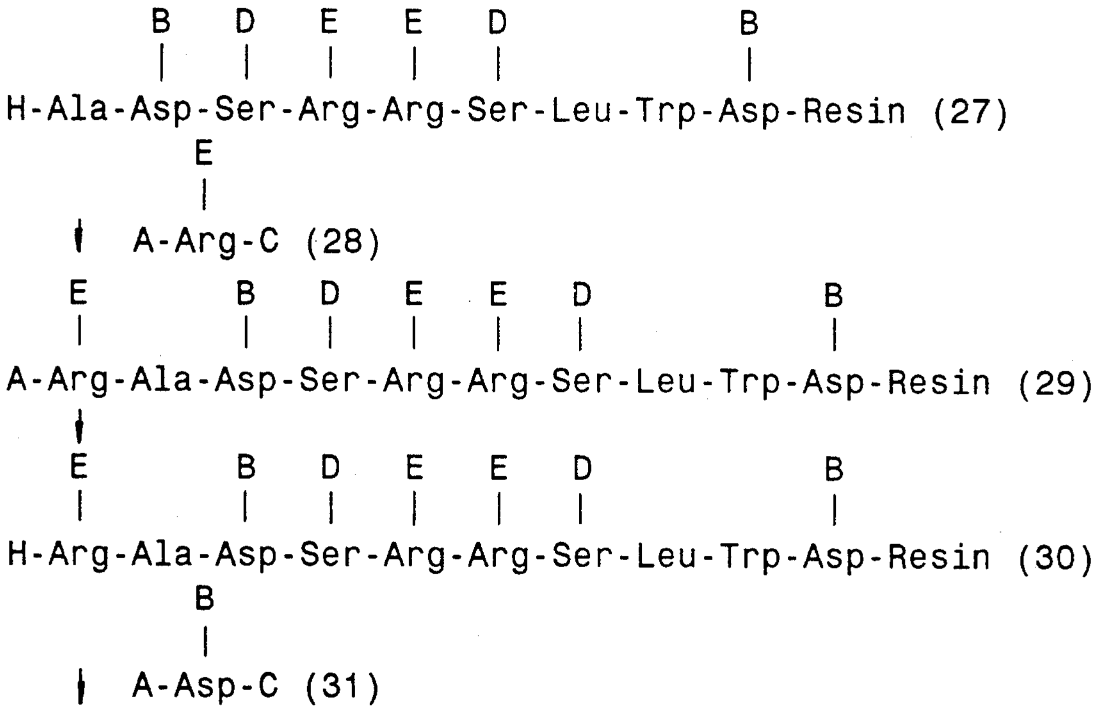
Figure 2D:
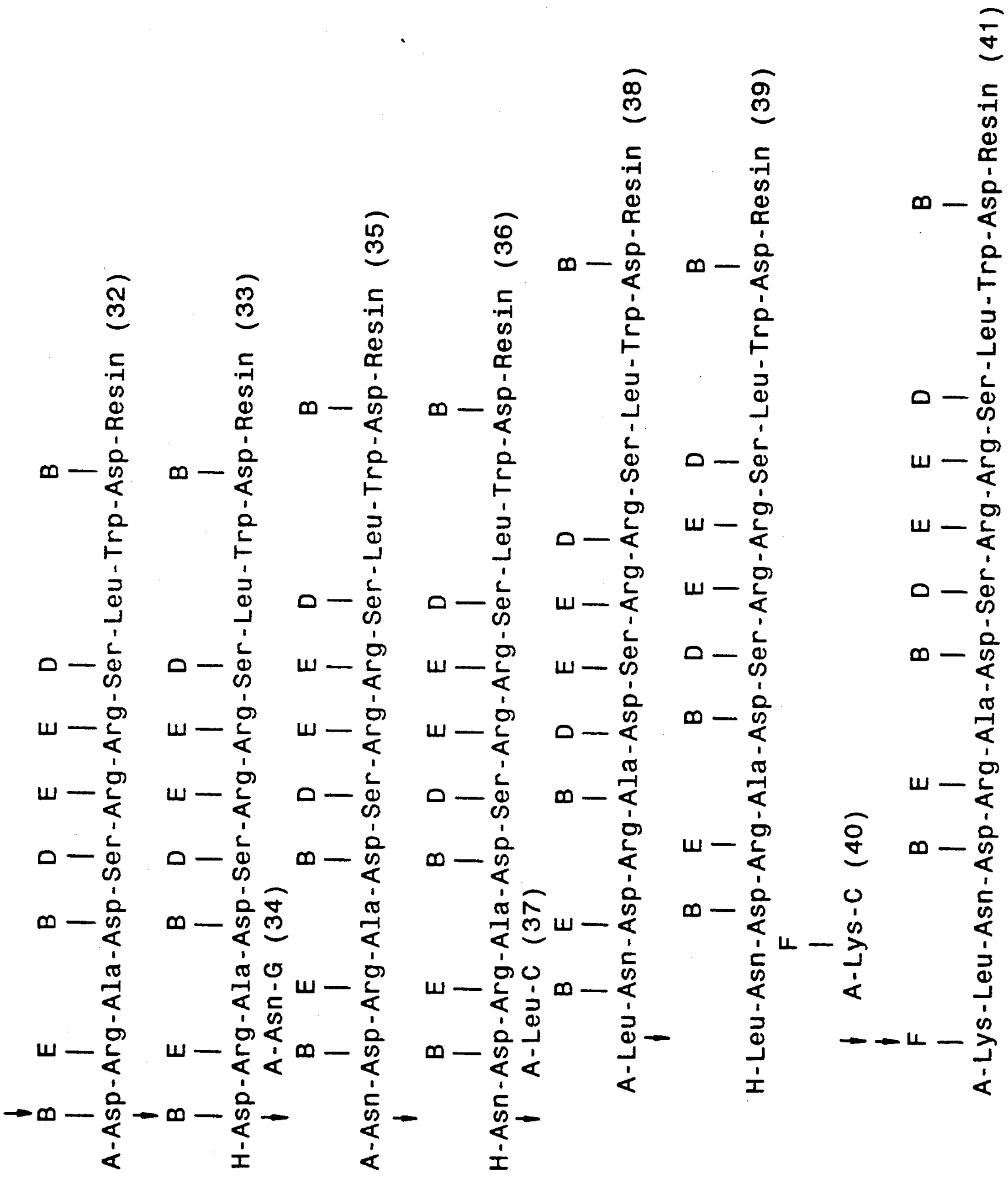
Figure 2E:
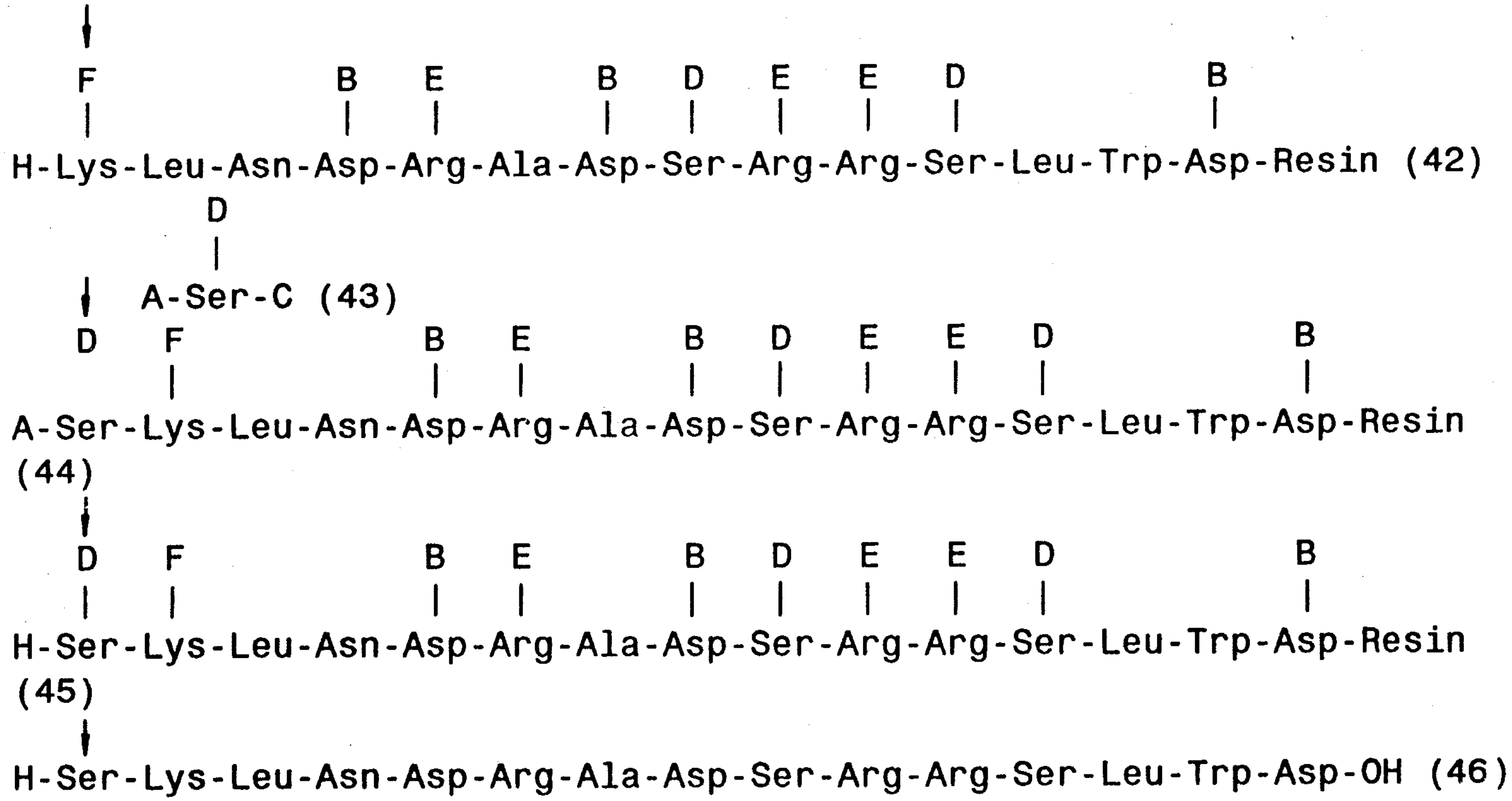

The present invention relates to a novel series of Leu3a binding peptides, to stabilized derivatives thereof, and to therapeutic and diagnostic applications of such peptides.

Preparation of Peptides

The Leu3a binding peptides of the invention may be prepared using conventional synthetic procedures, or by other procedures, including recombinant DNA techniques. When a synthetic method is used, the peptides may be synthesized in solution or on a solid support. Methods for solid phase synthesis are generally known to those of skill in the art, and various commercially available automatic synthesizers can be used in accordance with known protocols. See, for example, Stewart and Young, *Solid Phase Peptide Synthesis*, 2d Edition, Pearce Chemical Company, 1984; and Tam, et al., *J. Am. Chem. Soc.* 105:6442 (1983) and Merrifield, et al., *Biochemistry* 21:5020 (1982), which are incorporated herein by reference.

Preferably, however, either a 9-fluorenyl-methoxycarbonyl (Fmoc) or tert-butyloxycarbonyl (Boc) synthesis will be employed. Fmoc synthesis may be advantageously used when small quantities of peptide are desired; for large scale peptide preparations, the Boc procedure is preferred. A preferred method for Fmoc synthesis is described in Example II below.

Suitable protocols for Boc synthesis of selected peptides of the invention may be readily developed by those of skill in the art with aid of the present disclosure. In general, when the Boc procedure is used, the first amino acid of the desired peptide is coupled to a synthetic resin through its carboxyl group. The amino group of the first amino acid in the peptide is "blocked" by the substitution of a Boc group. During a subsequent step in the procedure, the Boc group is removed by treatment with trifluoroacetic acid (TFA), and the resulting amino group forms a peptide bond with a reactive carboxyl group of a second Boc amino acid in the presence of a suitable coupling agent. The process is repeated until the synthesis of the desired peptide is completed.

Of course, when using the Boc procedure, it is desirable to protect reactive side chains of the amino acids to prevent undesirable side reactions. Suitable side chain protecting groups can include Tos for arg; chlorobenzyloxycarbonyl for lys; benzyl for ser or thr; benzyl ester for asp; or others known to those of skill in the art.

After synthesis, the side chain protecting groups of the synthetic peptide may be deprotected and the peptide cleaved from the resin simultaneously by addition of, for example, hydrofluoric acid (HF) under conditions of low temperature (generally from about 0° C. to −20° C.). The hydrofluoric acid may contain scavengers such as anisole or thioanisole, p-thiocresol, and dimethylsulfide. After deprotection and cleavage, the HF and other volatile components are removed under vacuum, and the resin and peptide are rinsed with an organic solvent such as an ethyl ether. The peptide may be then separated from the resin by dissolution in a carbonate containing buffer, such as ammonium carbonate or DMF and $H_2O$. As a final step, the peptides may be further separated, if desired, from the post resin mixture by conventional means such as high performance liquid chromatography (HPLC).

Peptides prepared by Fmoc synthesis, Boc synthesis, or any other suitable procedure may be aliquoted in predetermined amounts and stored in conventional manners, such as in aqueous solutions or, even more preferably, in a powder or lyophilized state pending use. If extended aqueous storage is contemplated, it will generally be desirable to include agents including buffers such as Tris or phosphate buffers to maintain a pH of 7.0 to 7.5. Moreover, it may be desirable to include agents which will inhibit microbial growth, such as sodium azide. For extended storage in an aqueous state it will be desirable to store the solutions at 4° C., or more preferably, frozen. Alternatively, peptide(s) stored in a lyophilized or powdered state may be stored virtually indefinitely, e.g., in metered aliquots that may be rehydrated with a predetermined amount of water (preferably distilled water) or buffer prior to use.

Selection of Leu3a Binding Peptides

With the guidance of the present disclosure, several procedures may be carried out in order to test whether a given peptide is suitable for use in the present invention. First, the peptide may be tested in accordance with the procedures set forth in Example II below to determine whether it exhibits the desired degree of Leu3a binding activity, for example, an $IC_{50}$ of less than about 100 μg/well. Moreover, in accordance with the invention, selected peptides exhibiting the desired binding activity may be demonstrated to possess the additional advantageous property of inhibiting gp120-CD4 interaction, using, for example, the cell fusion assay described by Lifson, et al., in Nature (1986) 323:725, or in the in vitro assay described by Reinherz, et al., W089/03222, which are incorporated herein by reference.

Use Of Peptides

In addition to the procedures described in the examples below, the novel peptides of the present invention may be used for a number of beneficial diagnostic and therapeutic procedures, both in vitro and in vivo. For example, Leu3a antibody is widely used to bind CD4 in a number of diagnostic tests, and the Leu3a binding peptides of the present invention may advantageously be used in such test procedures to demonstrate the specificity of Leu3a-CD4 interaction. In one such test, for example, an aliquot of blood from an individual is incubated with Leu3a antibody and, as a control, a second aliquot is incubated with a composition comprising Leu3a antibody and a Leu3a binding peptide of the present invention. The ability of the Leu3a binding peptide to competitively inhibit the Leu3a-CD4 binding will demonstrate the specificity of the Leu3a-CD4 binding reaction. Thus, the peptides may be employed advantageously in any of a number of conventional diagnostic techniques that utilize the Leu3a antibody, including flow cytometric techniques and immunoassay, for example, as described in Example I.

The peptides may also be employed in otherwise conventional methods for purifying Leu3a antibody, for example, affinity chromatography. In such an application, a selected Leu3a binding peptide (and preferably, a serum-stabilized Leu3a binding peptide) may be conjugated to a solid phase carrier molecule, such as a suitable preparation of cellulose, Sephadex, or other suitable matrix, and incubated with a source of Leu3a antibody, such as ascites fluid from a mouse that has been injected with a hybridoma that produces Leu3a or tissue culture medium in which such a hybridoma has been cultured. The Leu3a will bind to the peptide-solid phase carrier, thereby allowing its separation from soluble components of the ascites or culture medium. After washing, the Leu3a can be eluted from the carrier using various conventional procedures including titration with a source of the free, soluble peptide of the present invention.

The peptides may also be formulated into pharmaceutical compositions for administration in vivo, for example, in cases of HIV infection. In addition to the peptide compounds of the invention, pharmaceutical compositions of the invention may contain any of a number of suitable excipients and auxiliaries that facilitate processing or administration of the peptides. Suitable formulations for parenteral administration include but are not limited to aqueous solutions of the peptides or suspensions of peptide in water-dispersible form. Suitable excipients, for example, saline, other physiologic buffers, or other excipients known to those of skill in the art may be used. If desired, the formulations may also contain stabilizers or substances that increase viscosity, for example, sodium carboxymethyl cellulose, sorbitol, and/or dextran. Alternatively, in some cases, suspensions of the peptides may be administered in suitable lipophilic carriers such as vegetable oils and the like or liposomes.

For treatment, the peptides may be administered using a therapeutic regimen compatible with the particular formulation and therapeutic indication. In the usual case, the peptides may be most easily administered by parenteral administration. Alternatively, the peptides may be formulated as a component of an aerosol for intranasal or intrabronchial administration. The peptides may also be administered topically to the skin or eye, or orally, rectally, intravaginally, or intraurethrally, when treating disorders for which the agent is effective at those sites.

As described further below, with the aid of the present disclosure, those of skill in the art should be able to derive suitable dosages and schedules of administration for any of a number of effective compositions containing the peptides. Thus, pharmaceutical compositions within the scope of the invention include, for example, compositions where the peptide is contained in any amount effective to inhibit CD4-gp120 interaction. Some embodiments may contain a dosage of peptide in the range of 0.2 mg to 500 mg, more usually 1 mg to 100 mg, or, alternatively, a formulation comprising from 0.001% to 99%, preferably from 0.01% to 20%, by weight of the peptide. Although this is a preferred range, determination of the most effective amounts for treatment of each disorder for which the peptides may prove efficacious may be readily determined by those of skill in the art.

Although the invention has been described in terms of particular embodiments found or proposed by the inventor to comprise preferred modes for practice of the invention, in light of the present disclosure, numerous other embodiments can be realized without departing from the intended scope of the invention. For example, changes may be made in the peptides (for example, by conservative amino acid substitution, or other modification) or in methods of their use, without affecting in kind or amount the biological function. Likewise, additional utilities which depend on the presence of the peptides of the present invention, in combination with future remedies, treatments or other therapeutic regimes, e.g., anti-autoimmune activity or a depression of transplant rejection or graft versus host disease, may be expected and fall within the scope intended. These and other aspects of the invention may be more readily understood by reference to the Examples below.

EXAMPLE I

PEPTIDE SYNTHESIS

In a preferred embodiment, peptides are synthesized using a Biosearch Model 9600 peptide synthesizer with Fmoc/BOP chemistry. Using this procedure, Fmoc is used to "protect" the alpha amino group found on each amino acid. Fmoc is readily "deprotected" by organic amines such as piperidine. BOP [(benzotriazole-1-yloxy)tris(dimethylamino)phosphonium hexafluorophosphate is a coupling reagent that reacts with the amino terminally-protected amino acid to form an amino reactive symmetric anhydride or an HOBt (1-hydroxybenzotriazole) active ester in the presence of HOBt and N-methylmorpholine.

As shown in FIG. 1, to initiate the procedure, an Fmoc derivative of the C-terminal residue of a desired peptide is covalently attached to a synthetic resin (preferably, a 4-hydroxymethyl-benzyl alcohol polystyrene-divinylbenzene copolymer) chosen for its size and resistance to the reagents of the procedure. The amino acid-resin is then treated with piperidine (deblocking), which removes the Fmoc group from the alpha amino terminus of the amino acid. In a separate reaction vessel, an N-methylmorpholinium salt of the next Fmoc derivatized amino acid is activated to its acyloxyphosphonium salt by treatment with BOP and HOBt. The acyloxyphosphonium salt is then converted to equimolar amounts of either a symmetric anhydride or an HOBt active ester, and the complex mixture of salt, anhydride and ester are all delivered to the reaction vessel containing the amino acid coupled resin, where the Fmoc-amino acid is added to the growing peptide chain. The cycle is repeated until synthesis of the desired peptide is complete.

Certain amino acids contain side chains which must be protected prior to commencement of the synthetic protocol. Thus, so called side chain "protecting groups" may be introduced into the amino acids used for synthesis to preclude undesirable side-chain reactions from occurring during the synthetic procedure. For example, asp may be protected with a tert-butyl ester, ser and thr with a tert-butyl group; arg with a 4-methoxy-2,3,6-trimethylbenzenesulfonyl group; and lys with a t-butoxycarbonyl group. Other suitable protecting groups and protected amino acids are readily known to those of skill in the art and may be obtained from commercial sources, such as the Sigma Corporation, St. Louis, Mo.

Asparagine and glutamine are usually coupled as active esters rather than symmetric anhydrides in order to avoid degradation occurring during symmetric anhydride formation. Thus, the asn and gln added to the growing chain in the specific protocol described below were pentafluorophenyl esters.

After synthesis is completed, the synthetic peptide is released from the resin. A number of different techniques known to those of skill in the art may be used for this procedure; however, the selection of given technique will usually depend upon whether a fully deblocked or N-terminally blocked peptide is desired. In many cases, a fully deblocked peptide will be the desired end product of the synthesis, and the peptide will be freed from the resin by treatment with trifluoroacetic acid (TFA) or by treatment with TFA and trimethylsilyl bromide in the presence of scavengers, such as 1,2-ethanedithiol, anisole and/or thioanisole. The peptide may be purified further by any of a number of known procedures, including, for example, preparative high performance liquid chromatography. The precise protocol used for peptide synthesis and purification is provided below in considerable detail and is schematically depicted in FIG. 2A-F.

Five hundred milligrams of a p-alkoxybenzyl alcohol resin coupled to an Fmoc protected C-terminal amino acid was placed in the reactor vessel R2 of a Biosearch Model 9600 peptide synthesizer. A solid mass of two millimoles of each of the side-chain protected Fmoc-amino acid derivatives were sequentially placed in each of the appropriate amino acid reservoirs. Two millimoles BOP reagent and 2 millimoles HOBt were also added to each amino acid reservoir, except those containing asparagine and glutamine, which received 2 millimoles of pentafluorophenyl ester of the appropriate Fmoc-amino acid and 3 millimoles HOBt. DM (dimethylformamide) was placed in reagent bottles #34 and 190 53, DCM (dichloromethane) was placed in reagent bottle #54, and methanol was placed in reagent bottle #50. Equal volumes of DMF and DCM were added to reagent bottles #55 and #35. An appropriate volume of 0.2 M DMF solution of N-methyl-morpholine was placed in reagent bottle #33, and a 6:7:7 mixture of piperidine, DMF, and toluene was placed in reagent bottle #51.

Synthesis was started using the Biosearch FMOC-BOP driver program and proceeded as shown in FIG. 2A-F. In the case of subroutine #1 for arginine, a small modification was added to the standard subroutine program to compensate for the low solubility of arginine. Because of the low solubility and high viscosity of arginine, 2.5 ml of neat DMF was added further to the reaction mixture and the dissolution steps were elongated.

After the completion of synthesis, the peptide resin was dried in vacuo. To 500 mg of the peptide resin, 4.0 ml of TFA, 0.6 ml of thioanisole, 0.3 ml of ethanedithiol, and 0.1 ml of anisole were added, and the reaction mixture was stirred at room temperature for one (1) hour. Then, 0.7 ml of trimethylsilyl bromide was added and the reaction mixture was stirred for an additional two (2) hours at 0° C. The resin was removed by filtration and washed three times with a small volume of TFA. The filtrate was collected and the TFA was evaporated in vacuo maintaining the temperature below 40°

C. Anhydrous ethyl ether was added to the residual material, and the precipitate was collected by filtration, washed three times with anhydrous ethyl ether, then dried in vacuo.

The peptide was further purified from the preparation by reverse-phase high performance liquid chromatography using a D-ODS-5 column (i.d. 20 mm; length 250 mm:YMC Co., Ltd.). Separation was accomplished by elution with a linear gradient of from 20:80 acetonitrile:water to 60:40 acetonitrile:water, each containing 0.1% TFA. The peptide containing fraction was collected and lyophilized. For further purification, the peptides were subjected to a second HPLC purification and finally obtained as the trifluoroacetic acid salt.

EXAMPLE II

ASSAY OF SELECTED PEPTIDES

The Leu3a binding activity of peptides prepared as described above was demonstrated using a Leu3a competitive immunoassay. Generally, with this procedure, a source of CD4 (such as a membrane fraction from a CD4-expressing cell line) is immobilized on a solid matrix, and a suitable buffer is added. Then, aliquots of solutions containing labeled Leu3a and the peptide to be tested are added. Peptides having affinity for the Leu3a antibody will bind to the labeled Leu3a, and thereby prevent Leu3a from binding to the immobilized CD4. After a suitable period of incubation, the solid matrix is washed to remove unbound components and the labeled Leu3a bound is quantitated. In general, any of a number of conventionally labeled Leu3a preparations may be used, including radioactively labeled or enzyme-labeled Leu3a. However, a biotinylated Leu3a used in conjunction with an appropriate secondary reagent such as a complex of avidin-biotin-horseradish peroxidase is preferred. This secondary reagent specifically binds to the biotinylated Leu3a. A chromogenic substrate is added to the complex, enabling one to measure the amount of Leu3a bound as a function of absorbance.

The precise procedure used was as follows:

The cellular membrane fraction of MOLT4 cells or CCRF-CEM cells was used as a source of CD4 receptor. Two million cells, suspended in 2 ml of 40 mM HEPES (4-(2-hydroxyethyl)-1-piperazine ethanesulfonic acid) buffer (pH 7.4) containing 1 mM EGTA (ethylene-bis-(oxyethylene-nitrilo)-tetraacetic acid), 1 mM PMSF (phenylmethylsulfonylfluoride), 1,000 KIU/ml aprotinin and 150 mM sodium chloride, were lysed by two (2) successive 15 second cycles of ultrasonication and centrifuged at 100×g for five (5) minutes. The supernatant was collected and centrifuged at 15,000×g for ten minutes. The precipitate was resuspended in 1 ml of 50 mM sodium bicarbonate buffer, ultrasonicated by three (3) successive 15 second cycles, and mixed with 1 ml of 50 mM sodium bicarbonate buffer to obtain the cellular membrane suspension. Then, 50 μl of the membrane suspension was added to each well of a 96 well microtiter plate. After overnight incubation at 4° C., the buffer was removed and the adsorbed membrane fraction was fixed by addition of 50 μl of 10 mM PBS (phosphate buffered saline) containing 0.2% glutaraldehyde. After three (3) minutes at room temperature, the glutaraldehyde buffer was removed and the plates were washed five times with PBS. Then, 350 μl of PBS containing 2% bovine serum albumin (BSA) was added to each well to block subsequently added proteins from binding non-specifically to the plastic. After blocking at room temperature for one (1) hour, the blocking buffer was removed and the plates were washed five times with 0.2% BSA solution in PBS (BPBS).

The following dilutions of each peptide in BPBS—were prepared: 10 μg/ml; 20 μg/ml; 40 μg/ml; 100 μg/ml; 200 μg/ml, 400 μg/ml; 1 mg/ml and 2 mg/ml. A 50 μl aliquot of each dilution of a selected peptide was added to a well of a microtiter plate, together with 25 μl of a solution containing 600 ng/ml biotin-conjugated Leu3a (Becton Dickinson Immunocytometry Systems) in BPBS so that each well contained either 0.5, 1, 2, 5, 10, 20, 50 or 100 μg of peptide in a total volume of 75 μl. After overnight incubation at 4° C., the reaction mixture was removed and the plates were washed eight times with BPBS containing 0.05% Tween 20.

A solution containing a complex of avidin DH (reagent A) and biotinylated horseradish peroxidase H (reagent B) was prepared by adding 90 μl of reagent A and 90 μl of reagent B (ABC Kit:Vector Laboratories, Inc.) to 5 ml of BPBS containing 0.05% Tween 20.

Then, 50 μl of the enzyme complex solution was added to each well, and the plates were incubated at room temperature for four (4) hours. The reaction buffer was removed and the plates were washed eight times with 20 mM imidazole buffered saline containing 0.02% Tween 20. Equal volumes of substrate solution A (ABTS; 2,2'-azino-di[3-ethyl-benzthiazoline sulfonate]) and substrate solution B (hydrogen peroxide) (HybriClonal™ EIA Screening Kit: Kirkegaard & Perry Laboratories, Inc.) were mixed, and 100 μl of the substrate solution mixture was added to each well. After incubation at room temperature for one (1) hour, absorbance at 405 nm was measured by microplate reader model MPR-A4 (Tosoh Co., Ltd.).

Leu3a binding, as measured by absorbance, was calculated and plotted against peptide concentration to obtain a competitive inhibition curve. The $IC_{50}$ (concentration of peptide (μg/well) which inhibited Leu3a binding by 50%) for each peptide was calculated from such curves.

The results of testing CD4 (29-47), CD4 (38-67), CD4 (50-63), CD4 (49-62) and CD4 (49-63) using the assay are shown in Table III. CD4(38-67) and CD4(49-63) strongly inhibited Leu3a binding to CD4 from MOLT4 cells, but the other peptides tested did not. Surprisingly, even though CD4(49-63) is a relatively short peptide, containing only half the amino acids of CD4(38-67) CD4(49-63) possessed exceptionally strong inhibitory activity. CD4(50-63), which lacks serine at position 49, had very weak inhibiting activity and CD4 (49-62), which lacks aspartic acid at position 63, had very weak inhibiting activity.

TABLE III

| Properties of the CD4 Fragment Peptides | | | | | |
|---|---|---|---|---|---|
| | $IC_{50}$/well | [α]D | (C, °C.) | $Rf^{I}$ | $Rf^{II}$ |
| CD4 (38-67) | 4 | −62.71 | (0.7, 28) | 0.66 | 0.25 |
| CD4 (29-47) | 500 | −49.00 | (0.2, 25) | 0.74 | 0.31 |
| CD4 (49-63) | 10 | −43.50 | (0.2, 26) | 0.53 | 0.40 |
| CD4 (50-63) | >500 | −30.50 | (0.2, 24) | 0.60 | 0.17 |
| CD4 (49-62) | >500 | −42.00 | (0.2, 24) | 0.60 | 0.20 |

These results established that the minimum sequence of the active peptide was CD4(49-63). The specific rotation in 1 M acetic acid and the Rf values of the thin-layer chromatography of each peptide are also shown in Table III. For the latter procedure the following solvent systems were employed: $Rf^{I}$, 1-butanol:-pyridine:acetic acid:water=15:3:10:12; propanol:-pyridine:acetic acid:water=10:5:4:4.

EXAMPLE III

PREPARATION OF STABILIZED PEPTIDE DERIVATIVES

Degradation of peptides by proteases in blood or plasma may reduce or abrogate biological activity. Therefore, additional novel peptides that are more resistent to proteolytic degradation than the native peptides are also provided in accordance with the present invention. The following example demonstrates activity of those stabilized peptides in a Leu3a binding assay and enhanced stability in normal human serum.

Nine peptide analogues substituted with D-isomers at selected positions were synthesized and assayed for Leu3a binding activity, as described in Examples I and II, above. As shown in Table IV, substitution with the D-isomer at lys 50, ala 55, ser 57 and arg 58 and 59 did not affect inhibitory activity, and peptides substituted at three positions, such as [D-lys50, D-ala55, D-arg59]-CD4(49-63), also exhibited inhibitory activity.

TABLE IV

Properties of the D-Amino Acid-Substituted CD4 (49-63)

| | $IC_{50}$ μg/well | [α]d | (C, °C.) | $Rf^{I}$ | $Rf^{II}$ |
|---|---|---|---|---|---|
| [D-$Lys^{50}$,D-$Ala^{55}$]-CD4(49-63) | 36 | −37.50 | (0.2, 28) | 0.55 | 0.43 |
| [D-$Lys^{50}$,D-$Ala^{55}$,D-$Arg^{59}$]-CD4(49-63) | 25 | −30.00 | (0.2, 28) | 0.54 | 0.42 |
| [D-$Lys^{50}$,D-$Ala^{55}$,D-$Leu^{61}$]-CD4(49-63) | 22 | −25.50 | (0.2, 26) | 0.57 | 0.47 |
| [D-$Asn^{52}$,D-$Ala^{55}$]-CD4(49-63) | 60 | −28.50 | (0.2, 28) | 0.52 | 0.39 |
| [D-$Ala^{55}$]-CD4(49-63) | 32 | −37.50 | (0.2, 27) | 0.53 | 0.40 |
| [D-$Ala^{55}$,D-$Ser^{57}$]-CD4(49-63) | 10 | −42.50 | (0.2, 28) | 0.52 | 0.40 |
| [D-$Ala^{55}$,D-$Arg^{58}$]-CD4(49-63) | 36 | −30.00 | (0.2, 26) | 0.52 | 0.40 |
| [D-$Ala^{55}$,D-$Arg^{59}$]-CD4(49-63) | 23 | −30.76 | (0.13, 27) | 0.53 | 0.40 |
| [D-$Asp^{56}$]-CD4(49-63) | 56 | −47.50 | (0.2, 26) | 0.51 | 0.39 |

The specific rotation and Rf values of each peptide shown in Table IV were determined in a similar manner as set forth in Example II.

The substituted peptides were demonstrated to exhibit enhanced stability using a normal human serum degradation assay. For that assay, 0.5 ml of 50 μg/ml peptide in PBS was mixed with an equal volume of the serum, and the mixture was incubated at 37±1° C. for periods ranging from 0 to 24 hours. After incubation, the peptide was extracted from the serum and the extent of peptide degradation was determined.

Initially, three procedures for peptide extraction were investigated: ultrafiltration, acid-extraction, and solid extraction. However, the ultrafiltration method took about thirty minutes, during which degradation of peptide occurred. Recovery of peptide was very low by acid-extraction. Fortunately, the solid-phase extraction method gave excellent results, was very easy and rapid, and recovery of peptide was over 80%.

For solid-phase extraction, the reaction mixture was applied to a Sep-Pak $C_{18}$ cartridge immediately after incubation. The cartridge was washed with 2 ml of PBS, and the peptide was eluted from the cartridge with 2 ml of 50% acetonitrile in water containing 0.1% TFA, and the eluant was evaporated to remove acetonitrile and then lyophilized. The lyophilized material was dissolved in 1 ml of 0.1% TFA solution in water and analyzed by reverse phase high performance liquid chromatography using an AP-303/S-5 column (i.d. 4.6 mm; length 250 mm: YMC Co., Ltd.).

Initial attempts to measure degradation of synthetic CD4(49-63) using reverse phase HPLC at 215 nm failed to discriminate CD4(49-63) from degradation products, even if a variety of elution conditions were used. Therefore, an Fmoc group was not deblocked from the N-terminus of the peptide, and the resulting Fmoc peptide was analyzed by HPLC at 266 nm. This labeling procedure resulted in an achieve excellent resolution of peptide and serum-degraded materials and facilitated measurement of concentration of undegraded peptide.

The concentration of undegraded peptide was plotted against incubation time to obtain a degradation curve, and half-life of peptide in serum (the time point at which peptide recovery was 50% of that observed at 0 hr) was obtained from the curve. In one such experiment, the stability of an Fmoc-[D-$Lys^{50}$, D-$Ala^{55}$, D-$Arg^{59}$]-CD4(49-63) was compared with that of Fmoc-CD4(49-63) in the presence of normal human serum. Results are shown in Table V. The half life of the tri-substituted peptide was 2 hr in normal human serum, but the half life of its native counterpart was less than 30 minutes. Therefore, by D-isomer-substitution, the stability of this peptide in blood was increased significantly.

TABLE V

Stability of D-Amino Acid-Substituted CD4 (49-63) in Normal Human Serum

| | Half Life (hr.) |
|---|---|
| Fmoc-CD4 (49-63) | 0.5 |
| Fmoc-[D-$Lys^{50}$,D-$Ala^{55}$,D-$Arg^{59}$]-CD4 (49-63) | 2 |
| Half Life Improvement by D-Amino Acid Substitution | 4 |

Of course, although one highly stable Leu3a binding peptide was tested in this example, others may be synthesized, tested and selected in accordance with the procedures provided here.

The foregoing description of the invention has been directed to particular preferred embodiments in accordance with the requirements of the patent statutes and for purposes of explanation and illustration. It will be apparent, however, to those skilled in the art that many modifications and changes may be made without departing from the scope and the spirit of the invention.

What is claimed is:

1. A peptide or peptide salt consisting essentially of the amino acid sequence.

ser-lys-leu-asn-asp-arg-ala-asp-ser-arg-arg-ser-leu-trp-asp.

2. A peptide or peptide salt consisting of the amino acid sequence:

ser-lys-leu-asn-asp-arg-ala-asp-ser-arg-arg-ser-leu-trp-asp.

3. A pharmaceutical composition comprising the peptide or peptide salt of any one of claims 1 or 2 together with a pharmaceutically acceptacle excipient.

4. The peptide or peptide salt of any one of claims 1 or 2 including at least one D-amino acid.

5. The peptide or peptide salt of claim 4 including from one to four D-amino acids.

6. A pharmaceutical composition comprising the peptide or peptide salt of claim 4 together with a pharmaceutically acceptable excipient.

7. A peptide or peptide salt consisting essentially of the sequence;

ser-lys-leu-asn-asp-arg-ala-asp-ser-arg-arg-ser-leu-trp-asp 49 50 51 52 53 54 55 56 57 58 59 60 61 62 63 and wherein ala 55 is a D amino acid, or a pharmaceutically acceptable salt thereof.

8. A peptide or peptide salt consisting essentially of the sequence;

ser-lys-leu-asn-asp-arg-ala-asp-ser-arg-arg-ser-leu-trp-asp 49 50 51 52 53 54 55 56 57 58 59 60 61 62 63 wherein ala 55 and a second amino acid selected from the group consisting of ser, lys, leu, asn, arg, and trp are D-amino acids or pharmaceutically acceptable salts thereof.

9. A peptide or peptide salt consisting essentially of the sequence;

ser-lys-leu-asn-asp-arg-ala-asp-ser-arg-arg-ser-leu-trp-asp 49 50 51 52 53 54 55 56 57 58 59 60 61 62 63 wherein ala 55 and a second amino acid selected from the group consisting of lys 50, asn 52, ser 57, arg 58, and arg 59 are D-amino acids or pharmaceutically acceptable salts thereof.

10. A peptide or peptide salt consisting essentially of the sequence;

ser-lys-leu-asn-asp-arg-ala-asp-ser-arg-arg-ser-leu-trp-asp 49 50 51 52 53 54 55 56 57 58 59 60 61 62 63 wherein ala 5 and lys 50 are D-amino acids or pharmaceutically acceptable salts thereof.

11. A peptide or peptide salt consisting essentially of the sequence:

ser-lys-leu-asn-asp-arg-ala-asp-ser-arg-arg-ser-leu-trp-asp 49 50 51 52 53 54 55 56 57 58 59 60 61 62 63 wherein ala 55 and asn 52 are D-amino acids or pharmaceutically acceptable salts thereof.

12. A peptide or peptide salt consisting essentially of the sequence:

ser-lys-leu-asn-asp-arg-ala-asp-ser-arg-arg-ser-leu-trp-asp 49 50 51 52 53 54 55 56 57 58 59 60 61 62 63 wherein ala 55 and ser 57 are D-amino acids or pharmaceutically acceptable salts thereof.

13. A peptide or peptide salt consisting essentially of the sequence:

ser-lys-leu-asn-asp-arg-ala-asp-ser-arg-arg-ser-leu-trp-asp 49 50 51 52 53 54 55 56 57 58 59 60 61 62 63 wherein ala 55 and arg 58 are D-amino acids or pharmaceutically acceptable salts thereof.

14. A peptide or peptide salt consisting essentially of the sequence:

ser-lys-leu-asn-asp-arg-ala-asp-ser-arg-arg-ser-leu-trp-asp 49 50 51 52 53 54 55 56 57 58 59 60 61 62 63 wherein ala 55 and arg 59 are D-amino acids or pharmaceutically acceptable salts thereof.

15. A peptide or peptide salt consisting essentially of the sequence:

ser-lys-leu-asn-asp-arg-ala-asp-ser-arg-arg-ser-leu-trp-asp 49 50 51 52 53 54 55 56 57 58 59 60 61 62 63 wherein ala 55, lys 50 and arg 59 are D amino acids or pharmaceutically acceptable salts thereof.

16. A peptide or peptide salt consisting essentially of the sequence:

ser-lys-leu-asn-asp-arg-ala-asp-ser-arg-arg-ser-leu-trp-asp 49 50 51 52 53 54 55 56 57 58 59 60 61 62 63 wherein ala 55, lys 50 and leu 61 are D amino acids or pharmaceutically acceptable salts thereof.

17. A peptide or peptide salt consisting essentially of the sequence:

ser-lys-leu-asn-asp-arg-ala-asp-ser-arg-arg-ser-leu-trp-asp 49 50 51 52 53 54 55 56 57 58 59 60 61 62 63 and wherein asp 56 is a D amino acid or a pharmaceutically acceptable salt thereof.

* * * * *

UNITED STATES PATENT AND TRADEMARK OFFICE

CERTIFICATE OF CORRECTION

PATENT NO. : 5,171,838

DATED : December 15, 1992

INVENTOR(S) Yukinobu Chiba

It is certified that error appears in the above-indentified patent and that said Letters Patent is hereby corrected as shown below:

In Column 1, line 19, the phrase "CD4 molecule lymphocytes" should read --CD4 molecule on T-lymphocytes--.

Fig. 2F, Formula (47), on sheet 7 of 7, the formula should appear as follows:

```
"        D        "
         |
  Fmoc-Ser-C (47)
```

Column 10, line 39-40, the phrase "and 190 53" should read --and #53--.

Column 12, lines 29-30, "Hybri-Clonal TM" should read --Hybri-Clonal™--.

Column 13, line 2-3, the phrase "propanol:pyridine:acetic acid:water" should read --$Rf^{II}$, 1-propanol:pyridine:acetic acid:water--.

Column 15, lines 3-4, 9-10, 17-18, 25-26 and 31-32, and column 16, lines 1-2, 7-8, 13-14, 19-20, 25-26, and 32-33, the formulas which read
"ser-lys-leu-asn-asp-arg-ala-asp-ser-arg-arg-ser-leu-
trp-asp 49 50 51 52 53 54 55 56 57 58 59 60 61 62 63"

should read: (Note: The sequence numbers should appear directly below the corresponding amino acid designation.)

```
--ser-lys-leu-asn-asp-arg-ala-asp-ser-arg-arg-ser-leu-trp-asp--
   49  50  51  52  53  54  55  56  57  58  59  60  61  62  63
```

UNITED STATES PATENT AND TRADEMARK OFFICE

CERTIFICATE OF CORRECTION

PATENT NO. : 5,171,838

DATED : December 15, 1992

INVENTOR(S) : Yukinobu Chiba

It is certified that error appears in the above-indentified patent and that said Letters Patent is hereby corrected as shown below:

Column 15, line 27, the phrase "wherein ala 5" should read --wherein ala 55--.

Signed and Sealed this

Seventh Day of June, 1994

Attest:

BRUCE LEHMAN

Attesting Officer

Commissioner of Patents and Trademarks